United States Patent
Yoon et al.

(10) Patent No.: US 8,206,566 B2
(45) Date of Patent: Jun. 26, 2012

(54) ELECTROCHEMICAL MEASUREMENT SYSTEM FOR THE TRACE HEAVY METALS IN ORGANIC WASTE WATER

(75) Inventors: Jang-Hee Yoon, Busan (KR); Mi-Sook Won, Busan (KR)

(73) Assignee: Korea Basic Science Institute (KR)

( * ) Notice: Subject to any disclaimer, the term of this patent is extended or adjusted under 35 U.S.C. 154(b) by 161 days.

(21) Appl. No.: 12/840,066

(22) Filed: Jul. 20, 2010

(65) Prior Publication Data

US 2010/0282606 A1    Nov. 11, 2010

(30) Foreign Application Priority Data

Apr. 30, 2008 (KR) .................. 10-2008-0040403
May 14, 2008 (WO) ............... PCT/KR2008/002679

(51) Int. Cl.
*G01N 27/416* (2006.01)

(52) U.S. Cl. ........................................ 204/409; 205/789

(58) Field of Classification Search .................. 204/409, 204/411; 205/787, 789, 789.5
See application file for complete search history.

(56) References Cited

U.S. PATENT DOCUMENTS

| | | | | |
|---|---|---|---|---|
| 6,398,930 B2 * | 6/2002 | Fukunaga et al. | ............ | 204/409 |
| 6,544,393 B1 * | 4/2003 | Kunnecke | ...................... | 204/409 |
| 6,699,384 B1 * | 3/2004 | Lin et al. | ...................... | 205/792 |

FOREIGN PATENT DOCUMENTS

| | | |
|---|---|---|
| JP | 2002-181757 A | 6/2002 |
| JP | 2005-031050 A | 2/2005 |
| JP | 2005-283508 A | 10/2005 |

OTHER PUBLICATIONS

International Search Report / PCT?KR2008/002679.

* cited by examiner

*Primary Examiner* — Kaj K Olsen
(74) *Attorney, Agent, or Firm* — Park & Associcates IP Law, P.C.

(57) ABSTRACT

Disclosed herein is an electrochemical measurement system for analyzing heavy metals in organic compound-containing samples, comprising: a lower plate; a flow channel plate; an upper plate; an organic compound-decomposing electrode and a heavy metal analysis electrode; and a flow changeover portion. The disclosed system can continuously perform a pretreatment process for organic compound decomposition and a process for heavy metal analysis, thus making it possible to achieve the selective analysis and separation of heavy metals in wastewater. Also, it can substitute for expensive spectrophotometric analysis equipment and makes it possible to monitor trace heavy metals on-line in situ. In addition, it may include a small-sized battery as a power source, such that it is easy to carry and use.

14 Claims, 3 Drawing Sheets

ELECTROCHEMICAL MEASUREMENT SYSTEM FOR THE TRACE HEAVY METALS IN ORGANIC WASTE WATER

REFERENCE TO RELATED APPLICATIONS

This is a continuation of pending International Patent Application PCT/KR2008/002679 filed on May 14, 2008, which designates the United States and claims priority of Korean Patent Application No. 10-2008-0040403 filed on Apr. 30, 2008, the entire contents of which are incorporated herein by reference.

FIELD OF THE INVENTION

The present invention relates to a system for analyzing heavy metals in wastewater, and more particularly to an economical and efficient electrochemical analysis system for analyzing heavy metals in organic compound-containing samples, which allows a pretreatment process for organic compound decomposition and a process for heavy metal analysis to be performed continuously in one system.

BACKGROUND OF THE INVENTION

With the rapid development of industry and the urbanizing tendency of the population, the emission of large amounts of chemical hazardous substances becomes an important factor threatening the natural environment and ecosystem. Hazardous heavy metals, including arsenic (As), lead (Pb), cadmium (Cd), chromium (Cr), fluorine (F), selenium (Se) and mercury (Hg), adversely affect the human body, are not decomposed in water or converted into stable compounds and remain mixed and contaminate water and soil. If these hazardous heavy metals get into and accumulate in the body through various food routes such as via fish by proceeding up the food chain and are absorbed in vivo, they bind to biological substances to form non-biodegradable organic complexes, and thus are not quickly discharged out of the body and are accumulated in organs (e.g., liver or kidneys) or bone. Thus, these hazardous heavy metals can impair the health. Particularly, because heavy metals, once accumulated in the body, are not easily released, heavy metal pollution is a threatening factor and difficult to recover from.

The world health organization (WHO) strictly regulates the concentrations of various heavy metals which are hazardous to human health in drinking water to specific concentrations or less, and in order to prevent heavy metal pollution, countermeasures, including the regulation of pollutant emission, the improvement of pollutant treatment facilities, the development and growth of clean technology, and environmental education for social members, are performed.

However, in order to fundamentally prevent heavy metal pollution, a technology capable of accurately measuring the amounts of hazardous heavy metals emitted to the environment, must be ensured, and the strict regulation of environmental pollution must be performed using this technology.

Accordingly, the importance of the development of a technology for environmental prediction, monitoring and assessment is receiving great attention, and in order to meet the demand for novel environmental measurement procedures, to effectively cope with complicated, diversified environmental problems and ensure the assaying and analytic ability for generating compliance with international standards, studies focused on improving the reliability and accuracy of environmental measurement technology must be conducted.

In industrial plants causing industrial environmental wastewater, an effective process capable of reducing environmental pollution by monitoring environmental pollution through the accurate analysis of the content of heavy metals in wastewater can be ensured.

Wastewater from chemical industries, including petrochemicals, pulp industries, oil and fat industries, paper-making industries, petroleum purification processes, plastic industries and adhesive processes, which account for more than 27% of Korean industry, contain non-biodegradable organic compounds, including nitrobenzene, chlorophenol, benzidine and phenol. Such aromatic organic compounds are introduced into the human living environment, so that they are absorbed and concentrated in organisms and cause serious ecological problems in organisms. In addition, when the analysis of heavy metals in industrial wastewater is carried out, the accuracy of analytic results is reduced due to a matrix effect caused by the formation of metal complexes between heavy metals and organic compounds.

When hazardous heavy metal concentration in environmental wastewater containing such organic compounds is measured, it is difficult to measure accurate amounts due to the matrix effect, and for this reason, various studies focusing on increasing the accuracy of measurement have been conducted. Thus, in order to analyze hazardous heavy metals in wastewater containing organic compounds, the separation and treatment of the organic compounds must be performed before the analysis.

However, aromatic organic compounds are not readily degraded through low-cost biological methods, and in most cases they are degraded through separation methods, such as a precipitation method and a solvent extraction method, and chemical methods employing acids, alkalis or the like. However, such methods are excessively time-consuming and can reduce the accuracy of analysis due to the loss of samples, which can occur in pretreatment processes, and, in addition, they can cause secondary environmental pollution.

Thus, in order to develop a method for the analysis of heavy metals in industrial wastewater, studies on the effective pretreatment of non-biodegradable organic compounds and the selective separation and concentration of heavy metals after the pretreatment are required. Also, it is required to develop small-scale systems for conducting pretreatment, concentration and measurement, which can substitute for expensive spectrophotometric analytic instruments (e.g., UV-VIS spectrophotometers, atomic absorption spectrometers, ICP atomic emission spectrometers) and which can monitor trace heavy metals on-line in situ.

SUMMARY OF THE INVENTION

The present invention has been made in order to solve the above-described problems occurring in the prior art, and it is an object of the present invention to provide an economical and efficient electrochemical measurement system for analyzing organic compound-containing samples, which allows a pretreatment process for organic compound decomposition and a process for heavy metal analysis to be performed continuously in one system.

To achieve the above object, the present invention provides an electrochemical measurement system for decomposing organic compounds in wastewater and analyzing heavy metals in the wastewater, comprising: a lower plate having a channel plate-receiving portion formed in the upper side thereof; a flow channel plate, which is received in and coupled to the channel plate-receiving portion of the lower plate and includes, formed in the upper side thereof, an organic compound-decomposing channel, a heavy metal analysis channel and a discharge channel, and an organic compound decomposition electrode-receiving portion and a heavy metal analysis electrode-receiving portion, which communicate with the organic compound-decomposing channel and the heavy metal analysis channel, respectively; an upper plate, which is coupled to the lower plate and the upper side of the flow channel plate so as to seal the upper side of the channels; an organic compound decomposition electrode and a heavy metal analysis electrode, which are received in and coupled to the organic compound decomposition electrode-receiving portion and the heavy metal analysis electrode-receiving portion, respectively; and a flow changeover portion, comprising an on/off valve, which is provided at the upper side of the upper plate and coupled to one end of each of the organic compound-decomposition channel, the heavy metal analysis channel and the discharge channel so as to selectively open and close the wastewater outlet of each of the organic compound-decomposition channel and the heavy metal analysis channel, and an on/off switch for operating the on/off valve.

In the measurement system of the present invention, the lower plate is preferably formed of an aluminum material having an oxide layer formed on the surface thereof.

Also, the flow channel plate is formed of elastic synthetic resin, and preferably PDMS.

Preferably, the wastewater inlet of each of the organic compound-decomposing channel and the heavy metal analysis channel is formed in a circular shape, the wastewater outlet thereof is connected with the on/off valve, and the portion between the wastewater inlet and the wastewater outlet is formed in a curved shape consisting of continuously connected U shapes.

Moreover, preferably, the organic compound-decomposing electrode is received in and coupled to the organic compound decomposition-receiving portion, such that it comes in contact with wastewater introduced into the organic compound-decomposing channel, thus decomposing organic compounds in the wastewater. Particularly, the organic compound-decomposing electrode comprises: a body, which corresponds to the shape of the organic compound decomposition electrode-receiving portion and is coupled hermetically to the organic compound decomposition electrode-receiving portion; a decomposition electrode, which is provided at the lower end of the body so as to come in contact with wastewater; and a connector, which is electrically coupled to the decomposition electrode, extends through the upper side of the body and is connected with electrochemical measurement equipment.

Herein, the decomposition electrode is preferably made of any one selected from among a BDD (boron doped diamond) electrode, a Pt/Ti electrode, a carbon/carbon, a carbon/SUS (stainless steel) electrode, a carbon/platinum electrode and an Au/Fe electrode.

Also, preferably, the heavy metal analysis electrode is received in and coupled to the heavy metal analysis electrode-receiving portion so as to come in contact with wastewater introduced into the heavy metal analysis channel, thus analyzing heavy metals in the wastewater. Particularly, the heavy metal analysis electrode preferably comprises: a body, which corresponds to the shape of the heavy metal analysis electrode-receiving portion and is coupled hermetically to the heavy metal analysis electrode-receiving portion; an analysis electrode, which is provided at the lower end of the body so as to come in contact with wastewater; and a connector, which is electrically coupled to the analysis electrode, extends through the upper side of the body and is connected with electrochemical measurement equipment.

Herein, the analysis electrode preferably consists of a counter electrode made of Pt, a reference electrode of Ag/AgCl and a working electrode of BDDE (boron doped diamond electrode) or GCE (glassy carbon electrode). Also, preferably, the analysis electrode is formed in a shape corresponding to the shape of the lower end of the body, the length ratio of the counter electrode to the reference electrode is 2:1, and the working electrode having a circular shape is formed in the central portion of the counter electrode and the reference electrode.

Also, a pump for supplying wastewater to each of the channels at a specific rate is preferably provided adjacent to the inlet of each of the organic compound-decomposing channel, the heavy metal analysis channel and the discharge channel in the upper side of the upper plate.

In addition, a power source-receiving portion for receiving the on/off valve and the on/off switch and an on/off switch-receiving portion for receiving the on/off switch are preferably formed in the upper side of the lower plate.

Advantageous Effects

The electrochemical measurement system according to the present invention can continuously perform a pretreatment process for organic compound decomposition and a process for heavy metal analysis, thus making it possible to achieve the selective analysis and separation of heavy metals in wastewater. Also, it can substitute for expensive spectrophotometric analysis instruments JJV-VIS spectrophotometers, atomic absorption spectrometers and ICP atomic emission spectrometers, and makes it possible to monitor trace heavy metals on-line in situ. In addition, it may include a small-sized battery as a power source, such that it is easy to carry and use.

DESCRIPTION OF IMPORTANT REFERENCE NUMERALS USED IN THE DRAWINGS

Figure 1:
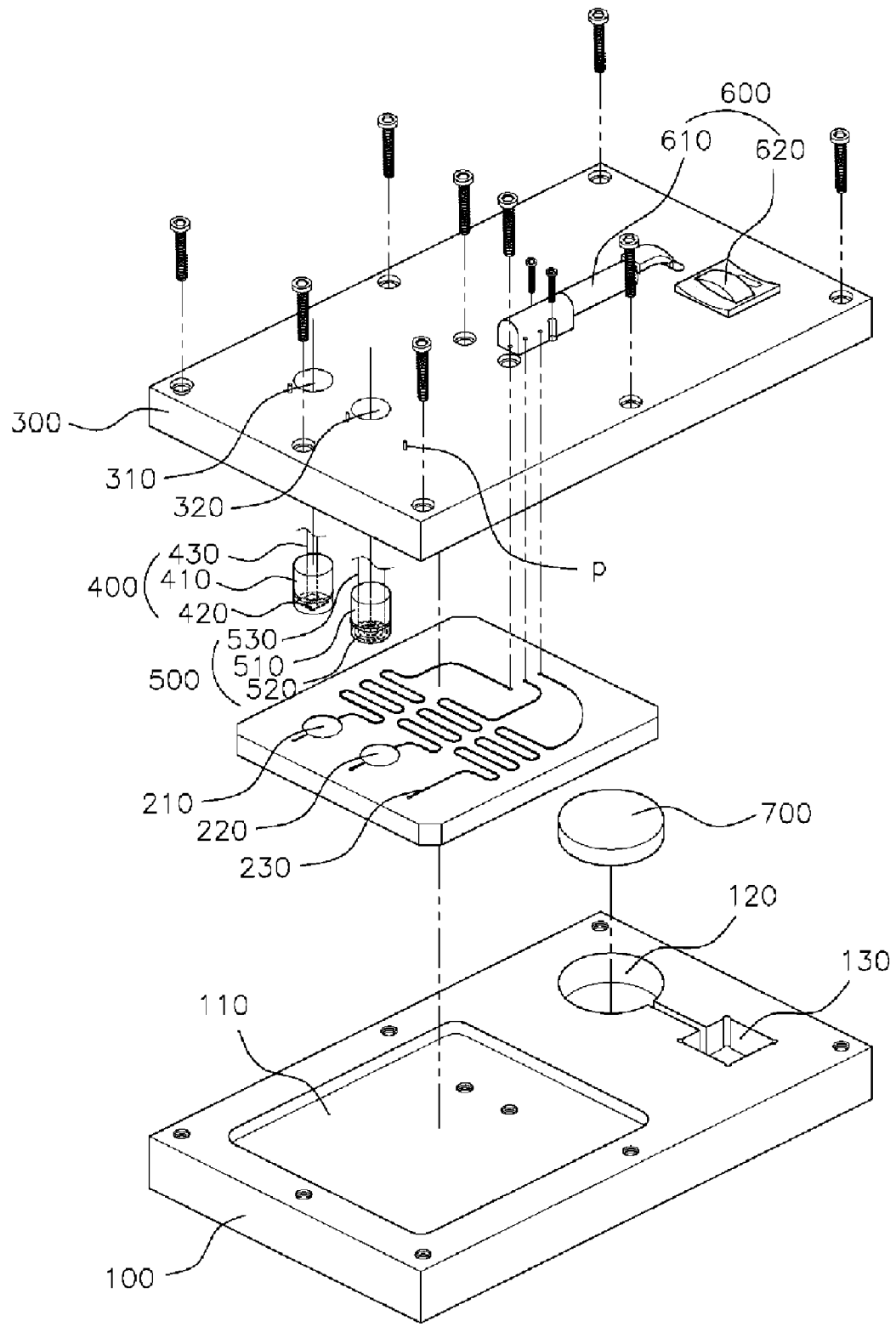
FIG. 1 is a perspective view showing the disassembled state of the inventive electrochemical measurement system for analyzing heavy metals in organic compound-containing samples.

100: lower plate
110: channel plate-receiving portion
120: power source-receiving portion
130: on/off switch-receiving portion
200: flow channel plate
210: organic compound-decomposing channel
220: heavy metal analysis channel
230: discharge channel
300: upper plate
310: organic compound decomposition electrode-receiving portion
320: heavy metal analysis electrode-receiving portion 400: organic compound decomposition electrode
410: body
420: decomposition electrode
430: connector
500: heavy metal analysis electrode
510: body
520: analysis electrode
530: connector
600: flow crossover portion
610: on/off valve
620: on/off switch
700: power source

DETAILED DESCRIPTION OF THE INVENTION

Hereinafter, a preferred embodiment of the present invention will be described in further detail with reference to the accompanying drawings.

Figure 2:
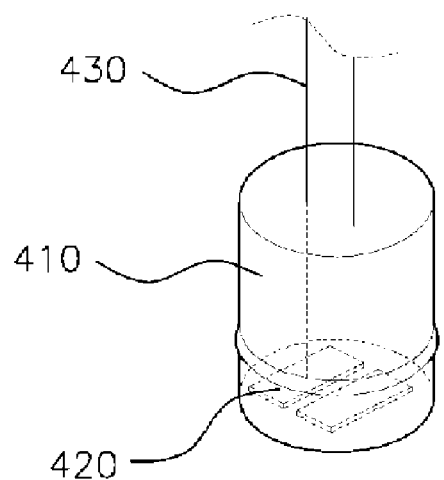
FIG. 2 is a perspective view of an organic compound decomposition electrode in the inventive electrochemical measurement system for analyzing heavy metals in organic compound-containing samples.

FIG. 1 is a perspective view showing the disassembled state of the inventive electrochemical measurement system for analyzing heavy metals in an organic compound-containing sample, and FIG. 2 is a perspective view of an organic compound decomposition electrode in the inventive electrochemical measurement system for analyzing heavy metals in an organic compound-containing sample.

As shown in FIGS. 1 and 2, the inventive electrochemical measurement system for analyzing heavy metals in an organic compound-containing sample is a system for decomposing organic compounds in wastewater and analyzing heavy metals in the wastewater and comprises a lower plate 100, a flow channel plate 200, an upper plate 300, an organic compound-decomposing electrode 400, a heavy metal analysis electrode 500 and a flow changeover portion 600.

The lower plate 100 will now be described.

The lower plate 100 is formed either of Teflon, which is physically and chemically stable and has excellent mechanical durability, or of alumina having an oxide layer formed on the surface thereof, and is in the form of a flat rectangular block. On the upper surface of the lower plate 100 is formed a channel plate-receiving portion 110 in which a flow channel plate 200 to be described later is received. The channel plate-receiving portion 110 has a rectangular shape and is formed in a depressed shape on the lower plate 100.

Also, in the upper side of the lower plate 100 is further formed a power source portion-receiving portion 120 in which a power source portion 700 for supplying power to an on/off valve 610 and an on/off switch 620. In addition, at the upper portion of the lower plate is formed an on/off switch-receiving portion 120 in which the on/off switch 620 is received. The power source portion-receiving portion 120 and the on/off switch-receiving portion 130 are formed in a concave shape in the lower plate 100, such that the power source portion 700, that is, a small-sized battery, is received in the power source portion-receiving portion 120 so as to supply power to the on/off valve 610 and the on/off switch.

Herein, the power source portion-receiving portion 120 conforms to the shape of the power source portion 700 for supplying power. If a small-sized battery is received in the power source portion-receiving portion 120, the measurement system of the present invention is used for portable applications, and if the measurement system of the present invention is not used for portable applications, an external power source can be used as the power source portion 700 to supply power.

The flow channel plate 200 will now be described.

The flow channel plate 200 is received in and coupled to the channel plate-receiving portion 110 of the lower plate 100, and at the upper side of the flow channel plate 200, flow channels, particularly an organic compound-decomposing channel 210, a heavy metal analysis channel 220 and a discharge channel 230, are formed. Each of the channels is formed by processing (e.g., etching) the flow channel plate 200, such that they are depressed from the surface of the flow channel plate 200.

The flow channel plate 200 is formed of elastic synthetic resin, such that the upper portion of the flow channel plate 200 is easily sealed hermetically through contact between each of the flow channels and the upper plate 300 to be described later. Preferably, the flow channel plate 200 is formed of polydimethylsiloxane (PDMS) having excellent processability and durability.

The flow channel plate 200 is slightly higher than the channel plate-receiving portion 110, such that the upper plate 3)0 is pressed down and elastically coupled to the upper portion of the flow channel plate 200, thus further increasing the sealing of each of the channels formed in the flow channel plate 200.

The organic compound-decomposing channel 210 and the heavy metal analysis channel 220 are formed in a circular shape at the wastewater inlet thereof, and the middle portions thereof are formed in curved shapes consisting of continuously connected U shapes, and the wastewater outlet is connected with an on/off valve 610 to be described later.

Namely, wastewater introduced into the wastewater inlet comes in contact with and reacts with an organic compound-decomposing electrode 400 and a heavy metal analysis electrode 300, and then organic compounds in the wastewater are decomposed and heavy metals in the wastewater are analyzed. Then, the wastewater, subjected to the organic compound decomposition and heavy metal analysis processes, flows to the wastewater outlet through the U-shaped channel and is discharged through a discharge channel 230.

Herein, the organic compound-decomposing channel 210 and the heavy metal analysis channel 220 are formed in a curved shape consisting of continuously connected U shapes, and this curved shape serves to delay the reaction between wastewater, introduced into the wastewater inlet, and the organic compound-decomposing electrode 400/heavy metal analysis electrode 500, such that wastewater is concentrated on and brought into contact with each of the electrodes, whereby the organic compound decomposition and heavy metal analysis processes are performed in an accurate manner.

Also, the wastewater, having undergone organic compound decomposition in the organic composition-decomposing channel 210 and the heavy metal analysis channel 220, is discharged through the discharge channel 230 to the outside.

In the process for decomposing organic compounds in wastewater, the on/off valve 610 is operated so as to cause the organic compound-decomposing channel 210 and the discharge channel to communicate with each other and so as to close the wastewater inlet of the heavy metal analysis channel 220. In the process for analyzing heavy metals in wastewater, subjected to organic compound decomposition, the on/off valve 610 is operated so as to cause the heavy metal analysis channel 220 to communicate only with the discharge channel 220. Each of the organic compound-decomposing process and the analysis process can also be repeated several times, and particularly, the organic compound-decomposing process is carried out such that wastewater is circulated several times through the organic compound-decomposing channel 210 and the discharge channel, such that organic compounds in the wastewater can be completely decomposed.

Preferably, a pump is further provided adjacent to the inlet of each of the organic compound-degrading channel 210, the heavy metal analysis channel 220 and the discharge channel, such that wastewater is supplied to each of the channels at a given flow rate. The pump is operated such that wastewater is supplied at a flow rate of about 0.02-12.3 m^/min.

Then, the upper plate 3)0 is formed in a rectangular shape and is coupled to the lower plate 100 and the upper side of the flow channel plate 200 to seal the upper side of the channels. The upper plate 3)0 is screwed to the upper side of the lower plate 100, such that the separation of the flow channel plate 200 is easily performed. On the upper side of the upper plate 3)0 is provided a pump (not shown; only an inlet "p", which is connected with the pump, is shown in FIG. 1) for supplying wastewater to the wastewater inlet of the channels, and on the upper side of the upper plate 3)0 are formed the on/off valve 610 and on/off switch 620 to be described later.

Also, at the wastewater inlet sides of the organic compound-decomposing channel 220 and the heavy metal analysis channel 220, an organic compound decomposition electrode-receiving portion 310 and a heavy metal analysis electrode-receiving portion are formed which communicate with the channels and receive an organic compound decomposition electrode 400 and a heavy metal analysis electrode 300.

Now, the organic compound decomposition electrode 400 will be described.

The organic compound decomposition electrode 400 is received in and coupled to the organic compound decomposition-receiving electrode 310, such that it comes in contact with wastewater introduced into the wastewater inlet of the organic compound-decomposing channel 210, thus providing for decomposition of organic compounds in the wastewater.

As shown in FIG. 2, the organic compound decomposition electrode 400 comprises: a body 400, which corresponds to the shape of the organic compound decomposition-receiving portion 310 and is hermetically coupled to the organic compound decomposition-receiving portion 310; a decomposition electrode 420, which is formed on the lower end of the body 410 and comes in contact with wastewater; and a connector 430, which is electrically connected with the decomposition electrode 420, extends through the upper side of the body 410 and is connected with electrochemical measurement equipment.

The body 410 of the organic compound decomposition electrode 400 is formed in the shape of the organic compound decomposition electrode-receiving portion 310, that is, a cylindrical shape, and has a rubber O-ring provided at the middle portion thereof, such that it is coupled hermetically to the organic compound decomposition electrode-receiving portion 310.

Also, the electrode 420 is provided at the lower end of the body 410, such that it comes in contact with wastewater to decompose organic compounds present in the wastewater. The electrode 420 consists of a positive (+) electrode and a negative (−) electrode. The (+) electrode and the (−) electrode are made of any one selected from among a BDD (boron doped diamond) electrode, a Pt/Ti electrode (an electrode consisting of platinum deposited on titanium), a carbon (glassy carbon) electrode and an Au/Fe electrode (an electrode consisting of gold deposited on iron). Preferably, the (+) electrode is made of carbon, and the (−) electrode is made of SUS or platinum. The electrode 420 electrolyzes organic compounds in wastewater to convert them into inorganic compounds (CO).

In a conventional process for analyzing heavy metals in wastewater, a pretreatment process for decomposing the organic compounds must be carried out before the analysis process in order to accurately analyze the heavy metals. However, in the present invention, a pretreatment process involving organic compound decomposition and a heavy metal analysis process are continuously performed in one system.

Furthermore, the connector 430 is electrically coupled to the decomposition electrode 420, and extends through the upper side of the body 410 and is connected with electrochemical measurement equipment, such that the degree of decomposition of organic compounds can be measured by checking either the total amount of carbon remaining after electrolysis in the decomposition electrode 420 or the concentration of produced carbon dioxide. Until the decomposition of organic compounds reaches a given level, wastewater is circulated through the organic composition-decomposing channel 210 and the discharge channel 230, such that the decomposition of the organic compounds is continuously performed.

Moreover, the heavy-metal analysis electrode 300 is received in and coupled to the heavy metal analysis electrode-receiving portion 320, such that it comes in contact with wastewater introduced into the heavy metal analysis channel 220, thus analyzing heavy metals in the wastewater.

Figure 3:
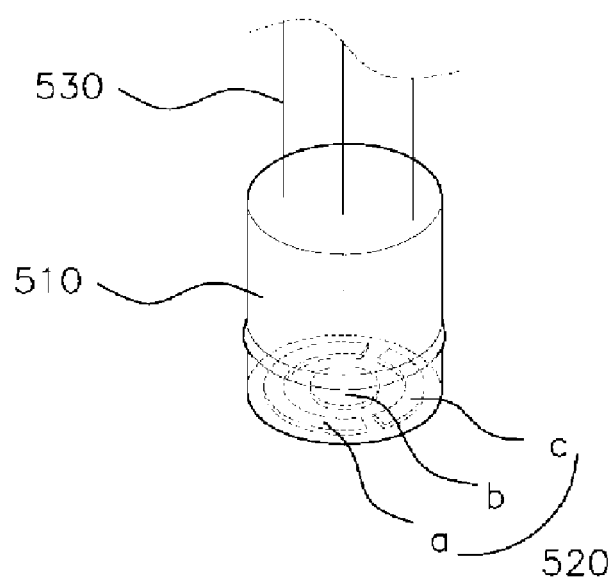
FIG. 3 is a perspective view of a heavy metal analysis electrode in the inventive electrochemical measurement system for analyzing heavy metals present in organic compound-containing samples.
Figure 4:
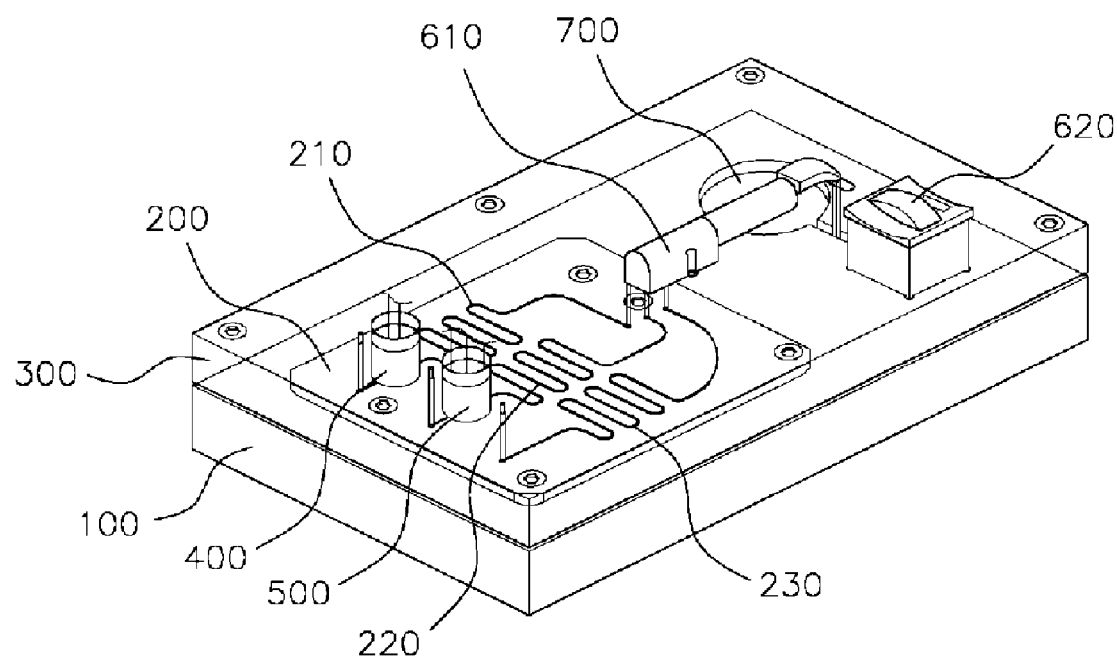
FIG. 4 is a perspective view of the inventive electrochemical measurement system for analyzing heavy metals present in organic compound-containing samples.

As shown in FIG. 3, the heavy metal analysis electrode 300 comprises: a body 510, which corresponds to the shape of the heavy metal analysis electrode-receiving portion 320 and is coupled hermetically to the heavy metal analysis electrode-receiving portion 320; an analysis electrode 520, which is formed at the lower end of the body 510 and comes in contact with wastewater; and a connector 530, which is electrically coupled to the analysis electrode 520, extends through the upper side of the body 510 and is connected with electrochemical measurement equipment.

The body 510 of the heavy metal analysis electrode 500 is formed in the shape of the heavy metal analysis electrode-receiving portion 320, that is, a circular shape, and has a rubber O-ring formed at the middle portion thereof, such that it is coupled hermetically to the heavy metal analysis electrode-receiving portion 320.

Also, the analysis electrode 520 is formed at the lower end of the body 510 and comes in contact with wastewater to analyze the amount of heavy metals in the wastewater. It consists of a counter electrode "a" made of a Pt plate or a spiral platinum wire, a reference electrode "c" made of an AgCl/Ag electrode (an electrode consisting of silver chloride deposited on silver), and a working electrode "b" made of BDDE or GCE. Also, it serves to measure the amount of heavy metals contained in wastewater.

Generally, the counter electrode must generally have a reaction area larger than that of the working electrode or the reference electrode. In consideration of this, the counter electrode, the working electrode and the reference electrode must be included in the heavy metal analysis electrode. The heavy metal analysis electrode 500 in FIG. 3 is designed in consideration of the area of the lower area of the circular body, such that each of the electrodes can perform heavy metal analysis in an efficient manner. Also, the heavy metal analysis electrode 500 is generally formed in a circular form corresponding to the shape of the lower end of the body.

Specifically, the counter electrode "a" is received in the lower end of the body 510 in order to efficiently analyze heavy metals, in a manner such that it is formed in a curved shape corresponding to the shape of the lower end of the body 510, the length ratio of the counter electrode "a" to the reference electrode "b" is 2:1, and the working electrode "c" having a diameter of 5 mm is formed in the central portion of the counter electrode.

Moreover, the connector 530 is electrically coupled to the analysis electrode 520, and extends through the upper side of the body 510 and is connected to electrochemical measurement equipment, such that the amount of heavy metals can be measured by checking the concentration of metal ions from the analysis electrode 520.

Then, the flow changeover portion 600 is provided at the upper side of the upper plate 3)0 and comprises: the on/off valve 610, which is connected to one end of each of the organic compound-decomposing channel 210, the heavy metal analysis channel 220 and the discharge valve 230 and selectively opens and closes the wastewater outlet of the channels; and the on/off switch 620 which operates the on/off valve 610. The on/off valve 610 and the on/off switch 620 receive power from the power source 700.

The on/off valve 610 consists of a known electronic valve and selectively opens and closes the wastewater outlet of each of the organic compound-degrading channel 210 and the heavy metal analysis channel 220 according to the operation of the on/off switch. In the process of decomposing organic compounds in wastewater, the on/off valve 610 closes the wastewater outlet of the heavy metal analysis channel 220 and opens the organic compound-decomposing channel 210 and the discharge channel so as to communicate with each other. In the process of analyzing heavy metals in wastewater, the on/off valve 610 closes the wastewater outlet of the organic compound-decomposing channel 210 and opens the heavy metal analysis channel 220 and the discharge channel 230 so as to communicate with each other.

INDUSTRIAL APPLICABILITY

As described above, according to the present invention, the pretreatment process for organic compound decomposition and the process for heavy metal analysis can be continuously performed in one system. Thus, the present invention can be applied in places or plants which require an efficient and economical process for analyzing organic wastewater.

What is claimed is:

1. An electrochemical measurement system for decomposing organic compounds in wastewater and analyzing heavy metals in the wastewater, comprising:
    a lower plate having a channel plate-receiving portion formed in the upper side thereof;
    a flow channel plate, which is received in and coupled to the channel plate-receiving portion of the lower plate and includes, formed in the upper side thereof, an organic compound-decomposing channel, a heavy metal analysis channel and a discharge channel, and an organic compound decomposition electrode-receiving portion and a heavy metal analysis electrode-receiving portion, which communicate with the organic compound-decomposing channel and the heavy metal analysis channel, respectively;
    an upper plate, which is coupled to the lower plate and the upper side of the flow channel plate so as to seal the upper side of the channels;
    an organic compound decomposition electrode and a heavy metal analysis electrode, which are received in and coupled to the organic compound decomposition electrode-receiving portion and the heavy metal analysis electrode-receiving portion, respectively; and
    a flow changeover portion, comprising an on/off valve, which is provided at the upper side of the upper plate and coupled to one end of each of the organic compound-decomposition channel, the heavy metal analysis channel and the discharge channel so as to selectively open and close a wastewater outlet of each of the organic compound-decomposition channel and the heavy metal analysis channel, and an on/off switch for operating the on/off valve.

2. The electrochemical measurement system of claim 1, wherein the lower plate is formed of an aluminum material having an oxide layer formed on the surface thereof.

3. The electrochemical measurement system of claim 1, wherein the flow channel plate is formed of elastic synthetic resin.

4. The electrochemical measurement system of claim 3, wherein the flow channel plate is formed of PDMS.

5. The electrochemical measurement system of claim 1, wherein a wastewater inlet of each of the organic compound-decomposing channel and the heavy metal analysis channel is formed in a circular shape, the wastewater outlet thereof is connected with the on/off valve, and the portion between the wastewater inlet and the wastewater outlet is formed in a curved shape consisting of continuously connected U shapes.

6. The electrochemical measurement system of claim 1, wherein the organic compound-decomposing electrode is received in and coupled to the organic compound decomposition-receiving portion, such that it comes in contact with wastewater introduced into the organic compound-decomposing channel, thus decomposing organic compounds in the wastewater.

7. The electrochemical measurement system of claim 6, wherein the organic compound-decomposing electrode comprises:
    a body, which corresponds to the shape of the organic compound decomposition electrode-receiving portion and is coupled hermetically to the organic compound decomposition electrode-receiving portion;
    a decomposition electrode, which is provided at the lower end of the body so as to come in contact with wastewater; and
    a connector, which is electrically coupled to the decomposition electrode, extends through the upper side of the body and is connected with electrochemical measurement equipment.

8. The electrochemical measurement system of claim 7, wherein the decomposition electrode is made of any one selected from among a BDD electrode, a Pt/Ti electrode, a carbon/carbon, a carbon/SUS electrode, a carbon/platinum electrode and an Au/Fe electrode.

9. The electrochemical measurement system of claim 1, wherein the heavy metal analysis electrode is received in and coupled to the heavy metal analysis electrode-receiving portion so as to come in contact with wastewater introduced into the heavy metal analysis channel, thus analyzing heavy metals in the wastewater.

10. The electrochemical measurement system of claim 9, wherein the heavy metal analysis electrode comprises:
    a body, which corresponds to the shape of the heavy metal analysis electrode-receiving portion and is coupled hermetically to the heavy metal analysis electrode-receiving portion;
    an analysis electrode, which is provided at the lower end of the body so as to come in contact with wastewater; and
    a connector, which is electrically coupled to the analysis electrode, extends through the upper side of the body and is connected with electrochemical measurement equipment.

11. The electrochemical measurement system of claim 10, wherein the analysis electrode consists of a counter electrode made of Pt, a reference electrode of Ag/AgCl and a working electrode of BDDE or GCE.

12. The electrochemical measurement system of claim 11, wherein the analysis electrode is formed in a shape corresponding to the shape of the lower end of the body, the length ratio of the counter electrode to the reference electrode is 2:1, and the working electrode having a circular shape is formed in the central portion of the counter electrode and the reference electrode.

13. The electrochemical measurement system of claim 1, wherein a pump for supplying wastewater to each of the channels at a specific rate is provided adjacent to the inlet of each of the organic compound-decomposing channel, the heavy metal analysis channel and the discharge channel in the upper side of the upper plate.

14. The electrochemical measurement system of claim 1, wherein a power source-receiving portion for receiving the on/off valve and the on/off switch and an on/off switch-receiving portion for receiving the on/off switch are formed in the upper side of the lower plate.

* * * * *